(12) United States Patent
Mazzell, Jr. et al.

(10) Patent No.: US 7,659,433 B2
(45) Date of Patent: Feb. 9, 2010

(54) PURIFICATION OF 1,1,1,3,3,3-HEXAFLUOROISOPROPANOL

(75) Inventors: Paul Mazzell, Jr., Aiken, SC (US); Joel Swinson, Evan, GA (US); Barry Jones, Martinez, GA (US); Daniel Graham, Martinez, GA (US)

(73) Assignee: Halocarbon Products Corporation, River Edge, NJ (US)

( * ) Notice: Subject to any disclaimer, the term of this patent is extended or adjusted under 35 U.S.C. 154(b) by 623 days.

(21) Appl. No.: 10/599,472

(22) PCT Filed: Feb. 4, 2005

(86) PCT No.: PCT/US2005/003366

§ 371 (c)(1),
(2), (4) Date: Nov. 3, 2006

(87) PCT Pub. No.: WO2005/077873

PCT Pub. Date: Aug. 25, 2005

(65) Prior Publication Data

US 2008/0058560 A1    Mar. 6, 2008

Related U.S. Application Data

(60) Provisional application No. 60/541,818, filed on Feb. 4, 2004.

(51) Int. Cl.
*C07C 29/145* (2006.01)
*C07C 29/82* (2006.01)
*C07C 29/80* (2006.01)

(52) U.S. Cl. .......... 568/881; 568/913; 568/914
(58) Field of Classification Search ............ 568/881, 568/913, 914

See application file for complete search history.

(56) References Cited

U.S. PATENT DOCUMENTS 3,702,872 A    11/1972    Regan

FOREIGN PATENT DOCUMENTS

GB            974 612        11/1964

OTHER PUBLICATIONS

Derwent Publications Ltd. 1994-252744; XP-002463629; Central Glass Co. Ltd. Jul. 5, 1994, Abstract.

*Primary Examiner*—Elvis O Price
(74) *Attorney, Agent, or Firm*—Norris McLaughlin & Marcus, P.A.

(57) ABSTRACT

1,1,1,3,3,3-Hexafluoroisopropanol (HFIP) substantially free of 1,1,1-trifluoroacetone (TFA) can be separated from a mixture containing both compounds by A) catalytic reduction with hydrogen followed by fractional distillation; B) cooling to a temperature at which HFIP freezes and TFA remains liquid; C) forming a high boiling complex comprising HF and TFA followed by fractional distillation; or D) producing HF-free conditions to yield a HFIP/TFA azeotrope followed by fractional distillation. It is emphasized that this abstract is provided to comply with the rules requiring an abstract, which will allow a searcher or other reader to quickly ascertain the subject matter of the technical disclosure. It is submitted with the understanding that it will not be used to interpret or limit the scope or meaning of the claims. 37 CFR § 1.72(b).

20 Claims, No Drawings

PURIFICATION OF 1,1,1,3,3,3-HEXAFLUOROISOPROPANOL

This application claims priority of U.S. Provisional Patent Application No. 60/541,818, filed on Feb. 4, 2004.

This invention relates to a process for purifying 1,1,1,3,3,3-hexafluoroisopropanol.

1,1,1,3,3,3-hexafluoroisopropanol (HFIP) is a clear, water-white liquid, which is soluble in water and many organic solvents. Because of its strong hydrogen bonding properties, HFIP can also be used as a solvent for many different types of polymers. HFIP is also used to prepare fluorinated esters of polyacrylate and polymethacrylate polymers, and to prepare synthetic pharmaceuticals.

HFIP can be prepared from 1,1,1,3,3,3-hexafluoroacetone (HFA) by catalytic reduction according to the following scheme:

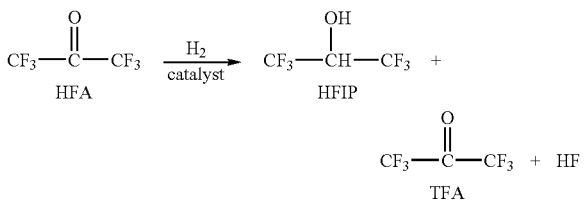

The hydrogenation catalyst is usually a nickel, palladium, ruthenium, rhodium or platinum metal, or a compound containing one or more of these metals. A byproduct of the catalytic reduction is 1,1,1-trifluoroacetone (TFA), which is very difficult to separate from the HFIP.

The present invention provides a first process for preparing 1,1,1,3,3,3-hexafluoroisopropanol substantially free of 1,1,1-trifluoroacetone. This first inventive process comprises the steps of:
 a) reducing 1,1,1,3,3,3-hexafluoroacetone with hydrogen in the presence of a first hydrogenation catalyst to produce a product mixture comprising 1,1,1,3,3,3-hexafluoroisopropanol and 1,1,1-trifluoroacetone; and
 b) preparing 1,1,1,3,3,3-hexafluoroisopropanol substantially free of 1,1,1-trifluoroacetone by subjecting the product mixture to a purification process comprising at least one purification step selected from the group consisting of:
  i) subjecting the product mixture to a further reducing with hydrogen in the presence of a second hydrogenation catalyst to yield a reduced product mixture, and separating 1,1,1,3,3,3-hexafluoroisopropanol substantially free of 1,1,1-trifluoroacetone from said reduced product mixture by fractional distillation;
  ii) cooling the product mixture to a temperature at which the 1,1,1,3,3,3-hexafluoroisopropanol freezes and the 1,1,1-trifluoroacetone remains liquid;
  iii) subjecting the product mixture, which, for the purposes of this purification step, further comprises a high boiling complex comprising hydrofluoric acid and 1,1,1-trifluoroacetone, to fractional distillation, and separating 1,1,1,3,3,3-hexafluoroisopropanol substantially free of 1,1,1-trifluoroacetone from said high boiling complex by said fractional distillation; and
  iv) subjecting the product mixture to hydrofluoric acid-free conditions wherein 1,1,1,3,3,3-hexafluoroisopropanol forms a high boiling azeotrope with 1,1,1-trifluoroacetone, and separating 1,1,1,3,3,3-hexafluoroisopropanol substantially free of 1,1,1-trifluoroacetone from said high boiling azeotrope by fractional distillation.

The reduction step (a) is carried out substantially as is well known in the art. The first hydrogenation catalyst can be any suitable catalyst provided, of course, that the reduction of the HFA produces a product mixture comprising both HFIP and TFA. As indicated above, catalysts useful in this regard include nickel, palladium, ruthenium, rhodium and platinum metal catalysts, and compounds containing one or more of these metals, for example, a palladium on carbon catalyst, particularly, a 2% palladium on carbon catalyst.

The product of the reduction step (a) is a product mixture comprising both HFIP and TFA. The TFA is initially present in such product mixture in an undesirable or significant amount. This product mixture will be subjected to purification process (b), and the result is that the TFA content will be reduced, and the HFIP can thereafter be recovered substantially free of TFA. By "substantially free of TFA" is meant that the HFIP will contain less than 500 ppm, less than 200 ppm or less than 100 ppm of TFA.

In a first purification process, the product mixture obtained from step (a), with or without intermediate work-up, is further reduced with hydrogen in the presence of a second hydrogenation catalyst to yield a reduced product mixture, and HFIP substantially free of TFA is separated from said reduced product mixture by fractional distillation. The conditions that are used to reduce HFA to HFIP and TFA can also be used to reduce the product mixture obtained from step (a), but the best results are obtained with elevated temperatures and longer contact times. The second hydrogenation catalyst is usually the same as the first hydrogenation catalyst as this is easier, but the second hydrogenation catalyst could be different from the first hydrogenation catalyst, if desired. For example, if the first hydrogenation catalyst is a palladium on carbon catalyst, particularly, a 2% palladium on carbon catalyst, the second hydrogenation catalyst may also be a palladium on carbon catalyst, particularly a 2% palladium on carbon catalyst, or else the second hydrogenation catalyst may be different from the first hydrogenation catalyst.

In a second purification process, the product mixture obtained from step (a), with or without intermediate work-up, is cooled to a temperature at which the HFIP freezes and the TFA remains liquid. HFIP has a high melting point (−4° C.) compared to TFA (−78° C.). HFIP substantially free of TFA can be obtained by cooling the product mixture obtained from step (a) to a temperature between about −4° C. and about −78° C. The frozen HFIP can be separated from the liquid TFA by any suitable method, for example, decantation, centrifugation, filtration, etc.

In a third purification process, it has been discovered that hydrofluoric acid (HF) forms a high boiling complex with TFA and some of the HFIP formed in step (a), and that HFIP substantially free of TFA can be separated from this high boiling complex by subjecting the product mixture containing the HFIP and the high boiling HF/TFA/HFIP complex to fractional distillation. As the reaction scheme depicted above makes clear, HF is ordinarily produced as a byproduct of the reduction of HFA. However, the amount of HF produced as a byproduct may be insufficient to separate from the HFIP the quantity of TFA on hand during the fractional distillation. In that event, additional HF can be introduced with the other reactants or separately added to the reduction step (a) and/or HF can be added to the product mixture obtained from step (a), with or without intermediate work-up, under conditions wherein at least some of the HF forms a high boiling complex with TFA and some of the HFIP formed in step (a), and HFIP substantially free of TFA is separated from said high boiling complex by fractional distillation. In one embodiment, the third purification process involves adding HF to the product mixture obtained from step (a) in a ratio of hydrofluoric acid:product mixture of from about 1:99 to about 1:19, so that the amount of HF is about 1 to about 5% by weight of the product mixture. In another embodiment, HF is introduced with the other reactants or separately added to the reduction step (a), and in this embodiment larger amounts of HF can be added if desired.

In a fourth purification process, the product mixture obtained from step (a) is subjected to HF-free conditions so that the HFIP forms a high boiling azeotrope with TFA, and HFIP substantially free of TFA is separated from said high boiling azeotrope by fractional distillation. The HF-free conditions can be established by any suitable technique well known in the art, for example, by filtration of the product mixture through silica or potassium fluoride.

It should be apparent that any of the foregoing techniques provide a means of separating a mixture of HFIP and TFA to achieve HFIP substantially free of TFA regardless of the source of the mixture. Accordingly, the present invention also relates to a second process for separating HFIP substantially free of TFA from a mixture of HFIP and TFA. This second inventive process comprises the steps of:

a) providing a mixture comprising 1,1,1,3,3,3-hexafluoroisopropanol and 1,1,1-trifluoroacetone; and b) preparing 1,1,1,3,3,3-hexafluoroisopropanol substantially free of 1,1,1-trifluoroacetone by subjecting the mixture to a purification process comprising at least one purification step selected from the group consisting of:

i) subjecting the mixture to a reducing with hydrogen in the presence of a hydrogenation catalyst to yield a reduced mixture, and separating 1,1,1,3,3,3-hexafluoroisopropanol substantially free of 1,1,1-trifluoroacetone from said reduced mixture by fractional distillation;

ii) cooling the mixture to a temperature at which the 1,1,1,3,3,3-hexafluoroisopropanol freezes and the 1,1,1-trifluoroacetone remains liquid;

iii) subjecting the mixture, which, for the purpose of this purification step, further comprises a high boiling complex comprising hydrofluoric acid and 1,1,1-trifluoroacetone, to fractional distillation, and separating 1,1,1,3,3,3-hexafluoroisopropanol substantially free of 1,1,1-trifluoroacetone from said high boiling complex by fractional distillation; and iv) subjecting the mixture to hydrofluoric acid-free conditions wherein 1,1,1,3,3,3-hexafluoroisopropanol forms a high boiling azeotrope with 1,1,1-trifluoroacetone, and separating 1,1,1,3,3,3-hexafluoroisopropanol substantially free of 1,1,1-trifluoroacetone from said high boiling azeotrope by fractional distillation.

This second inventive process is conducted in the same manner as hereinbefore described for the first inventive process.

For both the first inventive process and the second inventive process, the purification steps can be combined. In other words, the present invention also includes processes wherein two or more of steps (b)(i)-(b)(iv) are carried out.

The invention will now be described in more detail with reference to the following example:

EXAMPLE

A product mixture comprising HFIP, HF and a small amount of TFA is purified continuously according to the third purification process involving fractional distillation. The experimental parameters are as follows:

Experimental Parameters

| Column: | 3" by 20' |
| Pressure: | 40 psig |
| Dp: | 15" of $H_2O$ |
| Feed Rate: | 2 kgs/hr |
| HP in Feed: | 2% |

The results are as follows:

| % TFA in Feed | % TFA in Bottoms | % TFA in Overhead |
| --- | --- | --- |
| 0.2% | 2.2% | 0.009% |
| 0.2% | 2.4% | 0.013% |
| 0.2% | 2.8% | 0.041% |
| 0.2% | 2.9% | 0.025% |

It should be understood that the preceding is merely a detailed description of one or more embodiment(s) of this invention and that numerous changes to the disclosed embodiment(s) can be made in accordance with the disclosure herein without departing from the spirit or scope of the invention. The preceding description, therefore, is not meant to limit the scope of the invention. Rather, the scope of the invention is to be determined only by the appended claims and their equivalents.

What is claimed is:

1. A process for preparing 1,1,1,3,3,3-hexafluoroisopropanol substantially free of 1,1,1-trifluoroacetone, said process comprising the steps of:

a) reducing 1,1,1,3,3,3-hexafluoroacetone with hydrogen in the presence of a first hydrogenation catalyst to produce a product mixture comprising 1,1,1,3,3,3-hexafluoroisopropanol and 1,1,1-trifluoroacetone; and b) preparing 1,1,1,3,3,3-hexafluoroisopropanol substantially free of 1,1,1-trifluoroacetone by subjecting the product mixture to a purification process comprising at least one purification step selected from the group consisting of:

i) subjecting the product mixture to a further reducing with hydrogen in the presence of a second hydrogenation catalyst to yield a reduced product mixture, and separating 1,1,1,3,3,3-hexafluoroisopropanol substantially free of 1,1,1-trifluoroacetone from said reduced product mixture by fractional distillation;

iii) subjecting the product mixture, which, for the purposes of this purification step, further comprises a high boiling complex comprising hydrofluoric acid and 1,1,1-trifluoroacetone, to fractional distillation, and separating 1,1,1,3,3,3-hexafluoroisopropanol substantially free of 1,1,1-trifluoroacetone from said high boiling complex by fractional distillation; and iv) subjecting the product mixture to hydrofluoric acid-free conditions wherein 1,1,1,3,3,3-hexafluoroisopropanol forms a high boiling azeotrope with 1,1,1- trifluoroacetone, and separating 1,1,1,3,3,3-hexafluoroisopropanol substantially free of 1,1,1-trifluoroacetone from said high boiling azeotrope by fractional distillation.

2. The process according to claim 1, wherein the first hydrogenation catalyst is a palladium on carbon catalyst.

3. The process according to claim 2, wherein the palladium on carbon catalyst is a 2% palladium on carbon catalyst.

4. The process according to claim 1, wherein the product mixture is subjected to a purification process comprising subjecting the product mixture to a further reducing with hydrogen in the presence of a second hydrogenation catalyst to yield a reduced product mixture, and separating 1,1,1,3,3,3-hexafluoroisopropanol substantially free of 1,1,1-trifluoroacetone from said reduced product mixture by fractional distillation.

5. The process according to claim 4, wherein the second hydrogenation catalyst is a palladium on carbon catalyst.

6. The process according to claim 5, wherein the palladium on carbon catalyst is a 2% palladium on carbon catalyst.

7. The process according to claim 1, wherein the product mixture is subjected to a purification process comprising subjecting a product mixture further comprising a high boiling complex comprising hydrofluoric acid and 1,1,1-trifluoroacetone to fractional distillation, and separating 1,1,1,3,3,3-hexafluoroisopropanol substantially free of 1,1,1-trifluoroacetone from said high boiling complex by fractional distillation.

8. The process according to claim 7, which comprises adding hydrofluoric acid to the product mixture in a ratio of hydrofluoric acid:product mixture of from about 1:99 to about 1:19.

9. The process according to claim 7, wherein hydrofluoric acid is introduced along with the reactants or separately added to reduction step (a).

10. The process according to claim 1, wherein the product mixture is subjected to a purification process comprising subjecting the product mixture to hydrofluoric acid-free conditions wherein 1,1,1,3,3,3-hexafluoroisopropanol forms a high boiling azeotrope with 1,1,1-trifluoroacetone, and separating 1,1,1,3,3,3-hexafluoroisopropanol substantially free of 1,1,1-trifluoroacetone from said high boiling azeotrope by fractional distillation.

11. The process according to claim 10, wherein the hydrofluoric acid-free conditions are established by subjecting the product mixture to filtration through silica or potassium fluoride.

12. A process for separating 1,1,1,3,3,3-hexafluoroisopropanol substantially free of 1,1,1-trifluoroacetone from a mixture comprising 1,1,1,3,3,3-hexafluoroisopropanol and 1,1,1-trifluoroacetone, said process comprising the steps of:
 a) providing a mixture comprising 1,1,1,3,3,3-hexafluoroisopropanol and 1,1,1-trifluoroacetone; and
 b) preparing 1,1,1,3,3,3-hexafluoroisopropanol substantially free of 1,1,1-trifluoroacetone by subjecting the mixture to a purification process comprising at least one purification step selected from the group consisting of:
  i) subjecting the mixture to a reducing with hydrogen in the presence of a hydrogenation catalyst to yield a reduced mixture, and separating 1,1,1,3,3,3-hexafluoroisopropanol substantially free of 1,1,1-trifluoroacetone from said reduced mixture by fractional distillation;
  iii) subjecting the mixture, which, for the purposes of this purification step, further comprises a high boiling complex comprising hydrofluoric acid and 1,1,1-trifluoroacetone, to fractional distillation, and separating 1,1,1,3,3,3-hexafluoroisopropanol substantially free of 1,1,1-trifluoroacetone from said high boiling complex by fractional distillation; and
  iv) subjecting the mixture to hydrofluoric acid-free conditions wherein 1,1,1,3,3,3-hexafluoroisopropanol forms a high boiling azeotrope with 1,1,1-trifluoroacetone, and separating 1,1,1,3,3,3-hexafluoroisopropanol substantially free of 1,1,1-trifluoroacetone from said high boiling azeotrope by fractional distillation.

13. The process according to claim 12, wherein the mixture is subjected to a purification process comprising subjecting the mixture to a reducing with hydrogen in the presence of a hydrogenation catalyst to yield a reduced mixture, and separating 1,1,1,3,3,3-hexafluoroisopropanol substantially free of 1,1,1-trifluoroacetone from said reduced mixture by fractional distillation.

14. The process according to claim 13, wherein the hydrogenation catalyst is a palladium on carbon catalyst.

15. The process according to claim 14, wherein the palladium on carbon catalyst is a 2% palladium on carbon catalyst.

16. The process according to claim 12, wherein the mixture is subjected to a purification process comprising subjecting a mixture further comprising a high boiling complex comprising hydrofluoric acid and 1,1,1-trifluoroacetone to fractional distillation, and separating 1,1,1,3,3,3-hexafluoroisopropanol substantially free of 1,1,1-trifluoroacetone from said high boiling complex by fractional distillation.

17. The process according to claim 16, which comprises adding hydrofluoric acid to the mixture in a ratio of hydrofluoric acid:mixture of from about 1:99 to about 1:19.

18. The process according to claim 16, wherein the mixture already comprises hydrofluoric acid.

19. The process according to claim 12, wherein the mixture is subjected to a purification process comprising subjecting the mixture to hydrofluoric acid-free conditions wherein 1,1,1,3,3,3-hexafluoroisopropanol forms a high boiling azeotrope with 1,1,1-trifluoroacetone, and separating 1,1,1,3,3,3-hexafluoroisopropanol substantially free of 1,1,1-trifluoroacetone from said high boiling azeotrope by fractional distillation.

20. The process according to claim 19, wherein the hydrofluoric acid-free conditions are established by subjecting the mixture to filtration through silica or potassium fluoride.

* * * * *